(12) United States Patent
Woelfel et al.

(10) Patent No.: US 6,394,142 B1
(45) Date of Patent: May 28, 2002

(54) MULTI-LUMEN HOSE WITH AT LEAST ONE SUBSTANTIALLY PLANAR INNER PARTITION AND METHODS OF MANUFACTURING THE SAME

(75) Inventors: Mark E. Woelfel, Stockholm; Jack H. Britten, Blairstown, both of NJ (US)

(73) Assignee: Vital Signs, Inc., Totawa, NJ (US)

( * ) Notice: Subject to any disclaimer, the term of this patent is extended or adjusted under 35 U.S.C. 154(b) by 0 days.

(21) Appl. No.: 09/968,216

(22) Filed: Oct. 1, 2001

Related U.S. Application Data

(62) Division of application No. 09/672,205, filed on Sep. 28, 2000.

(51) Int. Cl.[7] ................................................. F16L 11/11
(52) U.S. Cl. ...................... 138/115; 138/116; 138/117; 138/121; 264/515; 264/286
(58) Field of Search ................... 138/115, 121, 138/116, 117; 264/514, 515, 286

(56) References Cited

U.S. PATENT DOCUMENTS

| | | | | |
|---|---|---|---|---|
| 4,064,355 A | * | 12/1977 | Neroni et al. | 138/115 |
| 4,096,887 A | * | 6/1978 | Streit | 138/115 |
| 4,654,962 A | * | 4/1987 | Ben-Dov | 138/115 |
| 4,795,439 A | * | 1/1989 | Guest | 138/115 |
| 5,305,797 A | * | 4/1994 | Roy, Sr. | 138/108 |
| 5,360,291 A | * | 11/1994 | Shimizu | 254/134.3 R |
| D405,522 S | * | 2/1999 | Hoenig et al. | D24/110 |
| 5,996,639 A | * | 12/1999 | Gans et al. | 138/115 |
| D424,687 S | * | 5/2000 | Hoenig et al. | D24/110 |
| 6,311,730 B2 | * | 11/2001 | Penza | 138/114 |

* cited by examiner

Primary Examiner—Patrick Brinson
(74) Attorney, Agent, or Firm—R. Gale Rhodes, Jr.

(57) ABSTRACT

A multi-lumen hose including a corrugated peripheral wall including an interior area and having an inner surface which defines a diameter, and at least one substantially planar inner partition extending from the inner surface across at least half of the diameter of the peripheral wall so as to divide the interior area into a plurality of lumen.

5 Claims, 5 Drawing Sheets

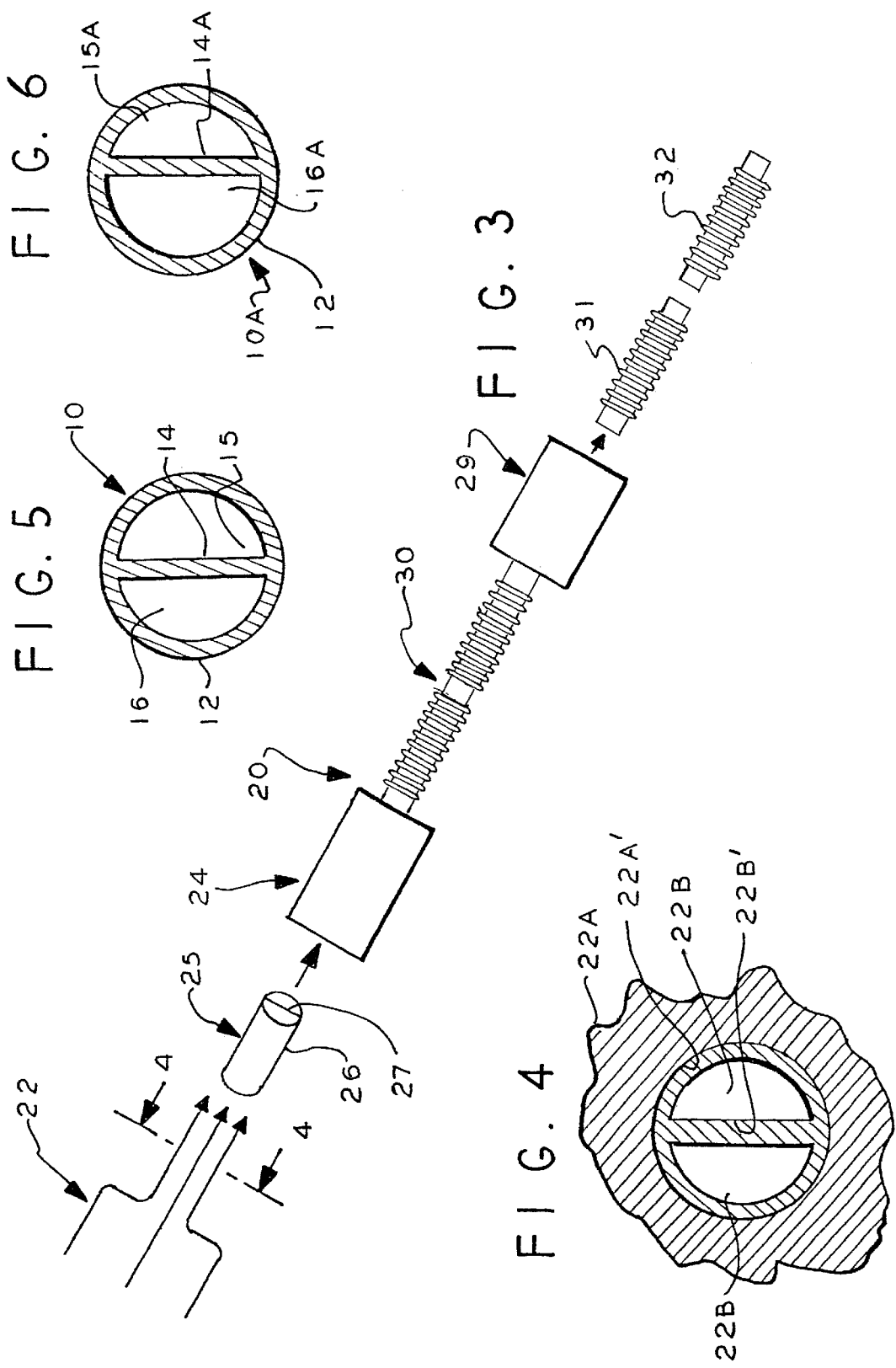

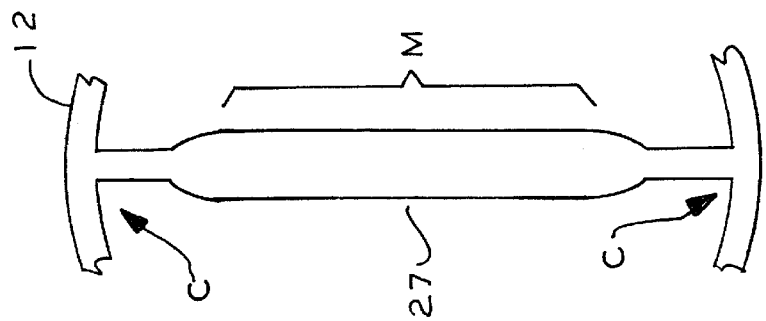
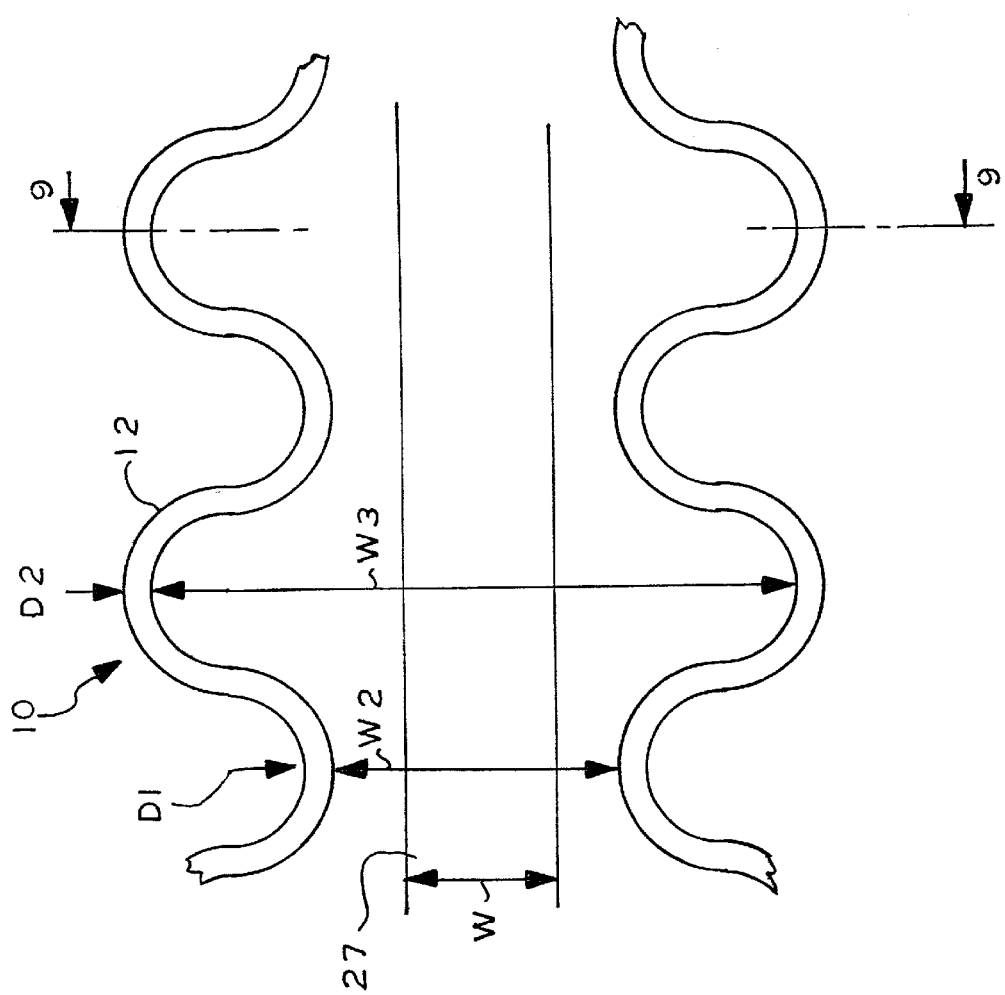

MULTI-LUMEN HOSE WITH AT LEAST ONE SUBSTANTIALLY PLANAR INNER PARTITION AND METHODS OF MANUFACTURING THE SAME

CROSS-REFERENCE TO RELATED APPLICATION

This application is a division of co-pending application Ser. No. 09/672,205, filed Sep. 28, 2000, entitled, MULTI-LUMEN HOSE WITH AT LEAST ONE SUBSTANTIALLY PLANAR INNER PARTITION AND METHODDS OF MANUFACTURING THE SAME, Mark E. Woelfel et al. inventors, and assigned to the same assignee as this application.

BACKGROUND OF THE INVENTION

This invention relates to multi-lumen hose having at least one inner planar partition dividing the hose into a plurality of lumen and to methods of manufacturing such hose.

Multi-lumen hose are known to the art and are used in many different applications including medical, commercial and industrial applications. For many of such applications, the peripheral wall of the hose is corrugated to provide the hose with greater flexibility and ease of use.

More particularly, this invention relates to multi-lumen hose, and by way of example and not by way of limitation, dual-lumen hose of the type used to communicate anesthesia gas from an anesthesia machine or breathing gas such as oxygen, or oxygen enriched gas, from a ventilator, to a patient's mask or endotracheal tube, and thereby to the patient, and for communicating exhalation gas from the patient back to the anesthesia machine or ventilator. Flexible multi-lumen dual-lumen hose or tubing, sometimes referred to as dual passageway or dual air passageway, hose, tubing or connector pipe is disclosed in U.S. Pat. Nos. 5,121,746 and 5,996,639.

U.S. Pat. No. 5,121,746 entitled ANESTHETIC AND RESPIRATOR BREATHING CIRCUIT DEVICE, John R. Sikora inventor, patented Jun. 16, 1992, is incorporated herein by reference as if fully reproduced herein. The Sikora patent, FIGS. 3 and 4, discloses a multi-passage or lumen flexible connector pipe (hose) 30 including outer walls 22 and 21 and an inner wall, or inner partition, 25 dividing the pipe into passages or lumen 31 and 32. As shown in FIGS. 1–4, the outer walls of the pipe 30 are shown to be corrugated, and the inner wall or partition 25 also is shown to be corrugated. The Sikora patent teaches in connection with FIGS. 1 and 2 that anesthesia gas from the anesthetic machine 8 is communicated to the patient's mask 11 through the passage or lumen 32 provided in the pipe 30 and that exhalation gas from the patient's mask 11 is communicated back to the anesthetic machine through the passageway 31 formed in the pipe 30. In connection with FIGS. 2 and 3, the Sikora patent teaches that breathing gas, such as an enriched gaseous mixture of oxygen, is communicated to the patient's mask 11 through the passage or lumen 32 formed in the connector pipe 30 and that exhalation gas from the patient's mask 11 is communicated back to the respirator 15 through the passage or lumen 31 formed in the connector pipe 30. This patent also discloses that the corrugated dividing wall 25, FIG. 3, is a chordal dividing wall which divides the cross-section of the flexible tubular member into a larger and a smaller cross-section so as to provide first and second fluid flow paths of different sizes through the connector pipe or hose.

U.S. Pat. No. 5,996,639 entitled MULTIPLE COMPARTMENT CORRUGATED HOSE, Leo Gans et al., patented Dec. 7, 1999, is incorporated herein by reference as if fully reproduced herein. This patent teaches that it is an improvement over the multi-compartment hose disclosed in the Sikora patent and discloses a flexible multi-lumen hose including a corrugated peripheral wall and a corrugated inner partition. Specifically, as shown in FIG. 3 of this patent, the hose 10 includes a corrugated peripheral wall 20 and a corrugated inner partition 70 dividing the hose into two lumen 50 and 60 better seen in FIG. 1.

Design U.S. Pat. No. Des. 405,522 and U.S. Pat. No. Des. 424,687, patented Feb. 9, 2000 and May 9, 2000, respectively, disclose multiple embodiments of ornamental designs of breathing tubes for conveying oxygen or anesthesia gas to lungs and conveying exhaled gas away from lungs of a patient, Richard Hoeing inventor of both of these design patents, and these design patents are assigned to the same assignee as the present invention; these design patents are incorporated herein by reference as if fully reproduced herein.

Also known to the prior art are various ways of manufacturing corrugated hoses such as by the well-known continuous blow molding or vacuum assisted blow molding methods. One such manufacturing method, as noted in the incorporated U.S. Pat. No. 5,996,639 is described in U.S. Pat. No. 3,286,305 entitled APPARATUS FOR CONTINUOUS MANUFACTURE OF HOLLOW ARTICLES, P. H. Seckel inventor, patented Nov. 22, 1966, and which patent is incorporated herein as if fully reproduced herein.

In light of the foregoing background and prior art patents, it will be understood that this invention is particularly useful as flexible, multi-lumen hose or tubing of the type known to the art for communicating breathing or anesthesia gas to a patient and for communicating the patient's exhalation gas away from the patient. Such hose or tubing is sometimes referred to in the art as breathing tube, breathing circuit tubing, hose or connector pipe, and all such terms will be referred to hereinafter and in the appended claims as hose.

Accordingly, it is believed that there is a need in the art for a hose, particularly flexible corrugated hose, having at least one substantially planar inner partition dividing the hose into a plurality of lumen, and methods of manufacturing the same.

SUMMARY OF THE INVENTION

It is the object of the present invention to satisfy the foregoing need in the hose art.

A multi-lumen hose embodying the present invention may include a corrugated peripheral wall including an interior area and having an inner surface which defines a diameter; and at least one substantially planar inner partition extending from the inner surface across at least half of the diameter of the peripheral wall so as to divide the interior area into a plurality of lumen. A method of manufacturing a multi-lumen embodying the present invention may include the steps of forming a hot multi-lumen parison, said parison including a hollow cylindrical peripheral portion with an inner surface defining a diameter and at least one substantially flat planar partition extending from the inner surface and across at least half of the diameter of the peripheral portion, the inner partition dividing an interior area of said parison into a plurality of lumen; expanding the peripheral portion radially outward to cause the inner partition to expand in width and decrease in thickness medially and to decrease in thickness greater contiguously to the peripheral portion; and the greater decrease in thickness contiguously to the peripheral portion causing the inner partition to remain substantially planar upon expanding in width during radial expanding of the peripheral portion.

DESCRIPTION OF THE DRAWINGS

FIG. 3 is a diagrammatical illustration of the manufacturing method of the present invention and apparatus useful for practicing such manufacturing method;

FIG. 4 is a diagrammatical cross-sectional view taken generally along the line 4—4 in FIG. 3 in the direction of the arrows;

FIG. 5 is a diagrammatical cross-sectional view of a dual lumen hose embodying the present invention and provided with a diametrical substantially planar inner partition dividing the hose into two lumen of equal size;

FIG. 6 is a diagrammatical cross-sectional view, similar to FIG. 5 but showing an alternate embodiment of the present invention, including a chordal substantially planar inner partition dividing the hose into two lumen of different sizes, a larger lumen and a smaller lumen;

FIG. 8 is a diagrammatical illustration of the forming of the inner partition to be substantially planar as the outer peripheral wall is expanded radially outward and corrugated;

FIG. 9 is a cross-sectional view taken generally along the line 9—9 in FIG. 8 and in the direction of the arrows;

DESCRIPTION OF THE PREFERRED EMBODIMENT

Figure 1:
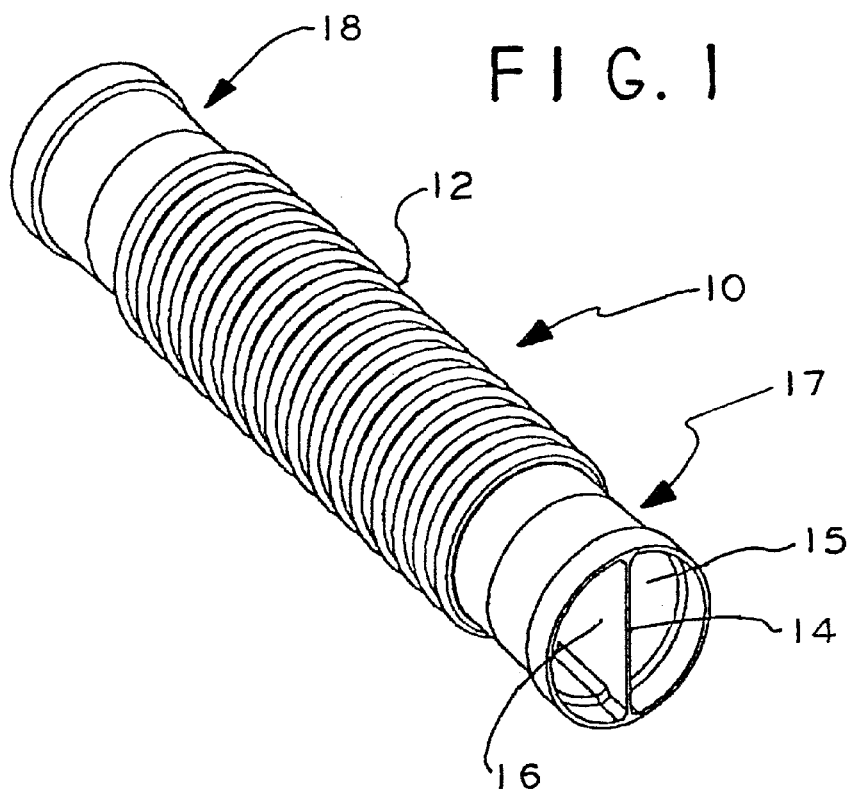
FIG. 1 is a perspective view of multi-lumen hose embodying the present invention and including at least one substantially planar inner partition.
Figure 2:
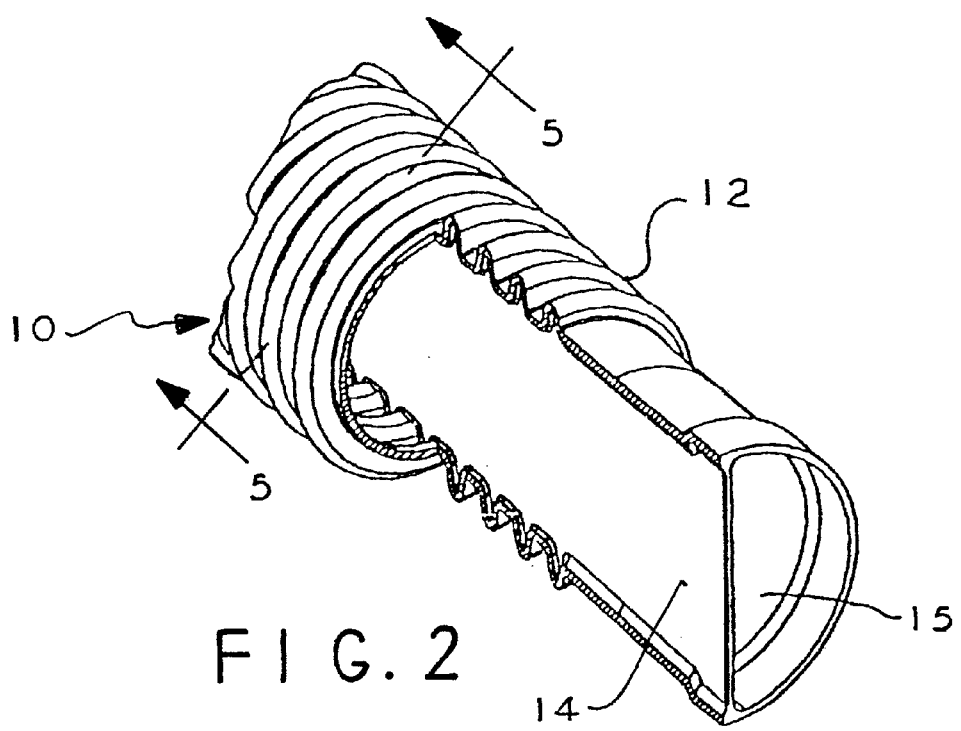
FIG. 2 is a partial view of FIG. 1 with a portion of the outer peripheral wall broken away to better show the substantially planar inner partition.

Referring to FIGS. 1 and 2, there is shown multi-lumen hose embodying the present invention and indicated by general numerical designation 10. In the embodiment shown in FIGS. 1 and 2, the multi-lumen hose is corrugated flexible multi-lumen hose but it will be understood that in accordance with the teachings of the present invention the multi-lumen hose of the present invention may not be corrugated although in the preferred embodiment it is corrugated. The hose 10 includes a corrugated peripheral wall 12 and an inner partition 14, better seen in FIG. 2 and sometimes referred to in the art as a septum, dividing the peripheral wall 12; or the interior area of the hose, into a plurality of lumen 15 and 16. It will be noted from FIG. 1, and particularly from FIG. 2, that the inner partition 14 is planar, or at least substantially planar.

As will be further understood from FIGS. 1 and 2, particularly FIG. 1, the multi-lumen hose of the present invention may be provided at its opposed end with cuffs indicated by general numerical designations 17 and 18 and which cuffs are of the type known to the art for facilitating interconnection of the multi-lumen hose to other devices or apparatus.

Referring to FIG. 3, there is shown a diagrammatical illustration of method of the present invention for continuously manufacturing the hose of the present invention. The apparatus utilized by such method includes a coextruder shown diagrammatically and indicated by general numerical designation 22, a corrugator shown diagrammatically and indicated by general numerical designation 24 and a cutter or cutting apparatus shown diagrammatically and indicated by general numerical designation 29. The coextruder 22 may be any coextruder known to the prior art for coextruding a hollow cylindrical outer peripheral wall from a first plastic material and for coextruding a planar, or substantially planar, inner partition from a second plastic material and which two coextrusions unite to form an integral extrusion, or what is sometimes referred to in the art as a parison or a hot plastic parison, and which parison is shown in FIG. 3, and indicated by general numerical designation 25. It will be understood that in such coextrusion the tubular member or outer peripheral 26 is coextruded from a first plastic material and the substantially planar inner partition 27 is coextruded form a second plastic material with the plastic materials uniting, fusing and melting together to produce an integral coextrusion, or parison 25, in the manner known to the coextrusion art. The coextruder 22 may be any suitable coextruder known to the art for producing the parison 25 described above and, which coextruders, as known to the art, include what is sometimes referred to in the art as a main extruder for extruding the tubular member or peripheral wall 26 from a first plastic material and another extruder, sometimes referred to in the art as the central or coextruder, for extruding the inner partition 27 from a different plastic material. The coextrusion dies of such main extruder and coextruder are shown diagrammatically in cross-section in FIG. 4 with the main extruder being indicated by numerical designation 22A and with the coextruder being indicated by numerical designations 22B—22B. As will be further understood from FIG. 4, the first plastic material extruded by the main extruder 22A is extruded through the main extruder die 22A' to produce a hollow cylindrical extrusion forming the tubular member or outer peripheral wall 26 of the parison 25 (FIG. 3) and the inner or central coextruder 22B—22B is provided with a generally rectangular die 22B' through which the substantially planar inner partition 27 (FIG. 3) of the parison 25 is extruded. Such main extruder may be, by way of example and not by way of limitation, a Thermatic main extruder available from the Davis-Standard company of Pawcatuck, Conn. The coextruder, by way of example and not by way of limitation, may be a coextruder of the Davis-Standard Company of Pawcatuck, Conn., Model DS125. It will be further understood in accordance with the teachings of the present invention, and referring again to the coextrusion or parison 25 of FIG. 3, that the tubular member or peripheral wall 26 may be coextruded from a blend of suitable plastic material, such as by way of example and not by way of limitation, a blend of about 91% polyethylene and about 9% EVA, and that the substantially planar inner partition coextrusion 27 may be coextruded from a suitable blend of plastic material, such as by way of example and not by way of limitation, a blend of about 81% polyethylene, about 19% EVA. As is known to those skilled in the art, EVA is more elastic than polyethylene, and hence it will be understood, and as is significant to the manufacturing method of the present invention and as set forth in detail below, the blend from which the substantially planar inner partition is extruded is more elastic than the blend from which the peripheral wall 26 is extruded.

Parison 25, FIG. 3, is fed continuously into the corrugator 24 which may be any suitable corrugator known to the art, such as for example the corrugators illustrated in FIGS. 5 and 6 of the incorporated U.S. Pat. No. 5,996,639 or, by way of further example and not by way of limitation, a corrugator available from Corma, Inc. of Toronto, Canada, Model 120HS, Vacuum. Corrugator 24 pulls the parison 25 forward and continuously corrugates AND EXPANDS the tubular member or outer peripheral wall 26 of the parison 25 to form or produce the corrugated peripheral wall 12 (FIG. 1) of the multi-lumen hose 10 of the present invention. As disclosed in incorporated U.S. Pat. No. 5,996,639, the outer peripheral wall 26 of the parison 25 (FIG. 3) may be corrugated and expanded radially outward continuously using a blow molding process by the corrugator apparatus and process taught in connection with FIG. 5 of this patent, and the outer peripheral wall 26 of the parison 25 may be continuously corrugated and expanded radially outward by the corrugating apparatus and process disclosed in FIG. 6 of this incorporated patent wherein such corrugation and expansion takes place continuously with the use of vacuum assisted blow molding process and apparatus. The manufacturing method process of the present invention for maintaining the substantially planar inner partition 27 of the parison 25 (FIG. 3) substantially planar, and to prevent it from becoming non-planar, rippling or wrinkling, while the outer peripheral wall 26 of the parison 25 is being expanded radially outward and corrugated, is taught in detail below.

And as known to the art, the corrugator 24 may also produce cuffs at predetermined spaced locations to provide opposed ends of the corrugated tubular member or peripheral wall with cuffs upon the corrugating tubing being cut by the cutter 29. After such corrugation the output from the corrugator 24 is fed continuously into a suitable cutter of the type known to the art for cutting plastic product that passes continuously therethrough. Such cutter may be any suitable cutter known to the art for cutting continuously moving plastic product and may be, by way of example and not by way of limitation, a cutter available from the Davis-Standard Company of Pawcatuck, Conn., Model DSC CTS.

The cutter 29 cuts the coextruded corrugated tubing 30 into discrete sections of multi-lumen flexible, corrugated hose, as indicated diagrammatically in FIG. 3, by numerical designations 31 and 32; In the manner known to the art, the cutter 29 cuts the corrugated tubing 30 where adjacent cuffs have been produced by the corrugator 24.

It will be understood from FIG. 4 that due to the configuration and disposal of the coextrusion die 22B—22B with respect to the main extruder die 22A, the substantially planar inner partition 27 of the parison 25 (FIG. 3) and therefore the substantially planar inner partition 14 (FIGS. 1 and 2) of the hose 10 of the present invention from which the substantially planar inner partition 14 is formed as taught in detail below, will be disposed diametrically with respect to the peripheral wall 26 of the parison 25 (FIG. 3) from which the corrugated outer peripheral wall 12 of the hose 10 of the present invention (FIG. 1) is made, to provide the multi-lumen hose 10 with the lumen 15 and 16, FIG. 1, of equal size. Alternatively, it will be understood that the coextruder die 22B—22B of FIG. 4 may be disposed other than diametrically with respect to the main extruder die 22A and may be, for example, disposed as a chord, other than a diameter, with respect to the main extruder die 22A and hence, as shown in the alternate multi-lumen hose embodiment 10A of FIG. 6, the multi-lumen hose of the present invention may be provided with a chordal, not diametrical, substantially planar inner partition so as to provide the hose 10A with a larger lumen 16A and a smaller lumen 15A.

The manufacturing method of the present invention will be described in the context of manufacturing the preferred embodiment of the multi-lumen hose 10 of the present invention shown in FIGS. 1 and 2 and described above. It will be understood that such manufacturing method is equally applicable to the manufacture of the alternate embodiment multi-lumen hose of the present invention shown in FIGS. 10–14. It will be understood that in the manufacture of these alternate embodiments the configuration of the main extruder 22A and coextruder 22B—22B shown in FIG. 4 would be configured to be complementary in shape to the multi-lumen hose alternate embodiments shown in FIGS. 10–14.

Figure 7:
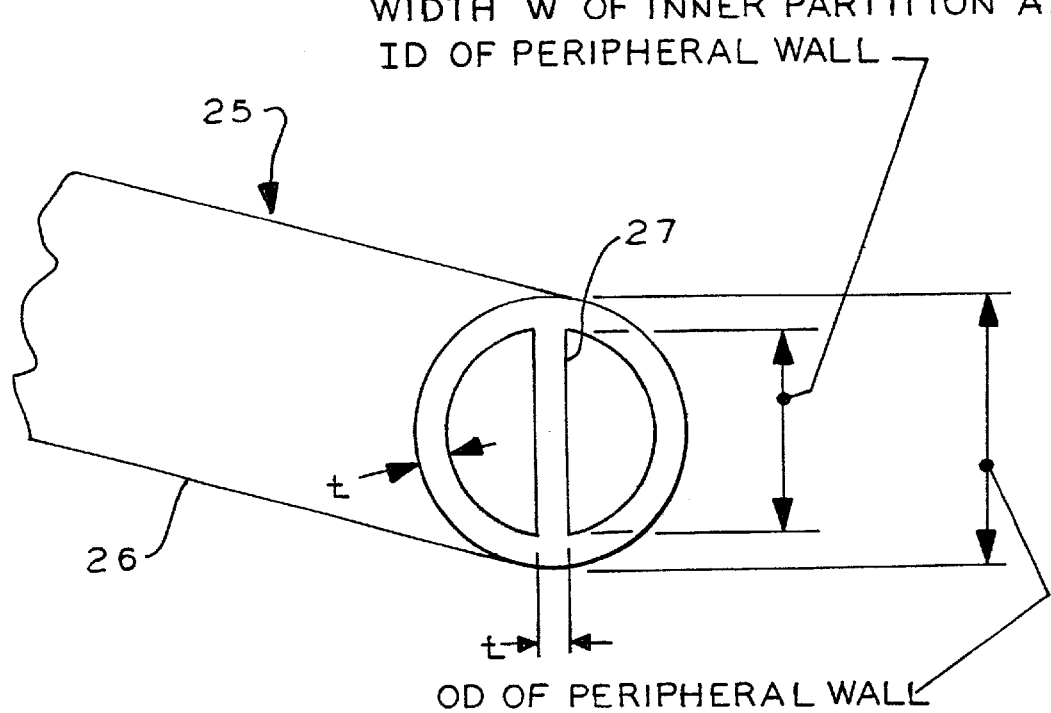
FIG. 7 is a partial diagrammatical illustration in perspective of a parison formed in the manufacturing process of the present invention.

A significant-feature of the manufacturing method of the present invention is the method by which the substantially planar inner partition 27 of the hot parison 25, FIG. 3, is maintained substantially planar during the radial outward expansion and corrugation of the parison peripheral wall 26, so as to form the inner partition 14 of the hose 10 shown in FIGS. 1 and 2 to be substantially planar in the end product of the multi-lumen hose of the present invention. The hot parison 25 (FIG. 3) from which the preferred embodiment of the multi-lumen hose 10 is formed is shown in FIG. 7. Referring to FIG. 7, the width W of the substantially planar inner partition 27 and the inner diameter, ID, of the peripheral wall 26 were about 0.50 inch. The thickness of both the inner partition 27 and the peripheral wall 26 was about 0.050 inch. The outer diameter, OD, of the peripheral wall 26 was about 0.60 inch.

Referring now to FIG. 8, a portion of the corrugated peripheral wall 12 of the multi-lumen hose 10 of FIGS. 1 and 2 is shown. From FIG. 8, it will be noted that the corrugated peripheral wall 12 includes alternating minimum and maximum corrugation diameters identified in FIG. 8 respectively as D1 and D2 which in this embodiment were about 0.83 inch and 1.05 inches respectively. It will be recalled that the outer peripheral wall 26 and the inner partition 27, FIG. 7, were coextruded into an integral parison and hence it will be understood that as the outer peripheral wall 26 of the parison 25 is being expanded radially outward and corrugated in the corrugator 24 to form the corrugated peripheral wall 12 of the hose 10 (FIGS. 1 and 2), as described above, the inner partition 27 of the parison 25, since it is formed integrally with the outer peripheral wall 26 of the parison 25, is expanded radially outward or increased in width as the parison peripheral wall 26 is expanded radially outward and corrugated. As illustrated in FIG. 8, the substantially planar inner partition 27 of the parison 25 (FIG. 7) is expanded from its original width W to an enlarged width W2 as the peripheral wall 26 is expanded radially outward and corrugated to form the minimum diameter D1 of the corrugated peripheral wall 12 of the hose 10. Additionally, it will be understood that the inner partition 27 is expanded in width from its original width W to a second larger expanded width W3 as the parison outer peripheral wall 26 is corrugated and expanded radially outwardly to provide the maximum diameter corrugations D2 identified in FIG. 8. Such outward expansion in width of the inner partition 27 will ordinarily cause the inner partition 27 to become non-planar and be provided with ripples or wrinkles as the inner partition 27 is expanded in width as it is pulled radially outwardly by the integrally formed peripheral wall 26 as it is expanded radially outwardly and corrugated. However, in accordance with the teachings of the present invention, the inner partition 27 remains substantially planar as it is expanded in width to increased widths W2 and W3, FIG. 8, due to the outward radial expansion and corrugation of the peripheral wall 26. It will be understood that as the inner partition 27 is increased in greater width to the widths W2 and W3 shown in FIG. 8, it will decrease in thickness upon being expanded in width and it has been discovered that by causing the inner partition 27 to decrease in thickness greater contiguously to the peripheral wall 26 than medially, the inner partition 27 will remain substantially planar during the outward radial expansion and corrugation of the peripheral wall 26 and that this will form the inner partition 14, FIGS. 1 and 2, to be a substantially planar inner partition. In FIG. 9, the greater decrease in thickness of the inner partition 14 contiguously to the peripheral wall 12 is indicated generally by the reduced cross-sectional area of the inner partition 14 identified by the general numerical designation C, and the lesser decrease in thickness of the inner partition 14 medially (the middle portion of the inner partition 14) is indicated diagrammatically by the middle portion of the inner partition 14 identified generally by the designation M. It will be understood that FIG. 9 is a diagrammatical illustration and that in actual shape the transition between the portion of the inner partition 14 contiguous to the peripheral wall 12 and the medial portion is a more gradual transition than shown. In the preferred embodiment illustrated in FIGS. 8 and 9, particularly FIG. 9, the inner partition 14 decreased from its original thickness of about 0.050 inch to about 0.010–0.012 inch at the portion C contiguous to the outer peripheral wall 12 and the medial portion of the inner partition 14 decrease from its original thickness of about 0.050 inch to about 0.24 inch medially at M.

It will be further understood in accordance with the teachings of the present invention that the greater decrease in thickness of the inner partition 14 contiguous to the peripheral wall 12 (at C in FIG. 9) than the decrease in thickness of the medial portion (at M in FIG. 9) of the inner partition 27 is produced by the inner partition of the parison 25 (FIG. 3) being sufficiently thick to cause the inner partition to decrease greater in thickness contiguously to the peripheral wall 12 than medially M as the inner partition is expanded in width from its original width W to the increased widths W2 and W3 shown in FIG. 8. More particularly, it will be understood that the inner partition 27 is thinned, or becomes thinner or decreases in width, as it is pulled outwardly, as viewed in FIG. 8, due to the peripheral wall 12 of the inner partition 14 being expanded radially outward and corrugated to form the peripheral wall 12 of the hose 10. By being formed sufficiently thick in accordance with the teachings of the present invention, the inner partition 14 will thin, or decrease in width locally contiguous (at C) in FIG. 9 to the corrugated peripheral wall 12 greater than it will thin or decrease in width in the middle or medially (at M) in FIG. 9.

It has also been discovered that by forming or extruding the inner partition 27 of the parison 25 (FIGS. 3 and 7) of a more elastic plastic material than the plastic material of which the peripheral wall 26 of the parison 25 is made, as described above, upon the inner partition 27 being expanded in width from its original width W to the increased widths W2 and W3 shown in FIG. 8, the inner partition 14 will decrease in thickness greater contiguously to the peripheral wall 12 (at C in FIG. 9) than it will decrease in thickness at its medial portion (at M in FIG. 9) as shown in FIG. 9.

It has been still further found that by practicing both of the aforementioned steps, i.e., making the inner partition 27 of the parison 25 sufficiently thick and by making the plastic of which the inner partition is formed more elastic than the plastic from which the peripheral wall is formed, these two steps together cause the inner partition 14 to decrease in thickness greater contiguously to the peripheral portion 12, at C in FIG. 9, than medially as indicated by the portion M in FIG. 9.

In the practice of the above-described methods of manufacturing of the present invention, and referring again to FIG. 3, the main extruder 22A (FIG. 4) was operated at a speed of about 20 rpm, the coextruder 22B—22B (FIG. 4) was operated at a speed of about 40 rpm and the corrugator 24 was operated at a speed of about 14–16 feet per minute.

It will be further understood that in accordance with the teachings of the present invention, the manufacturing method of the present invention may be used to produce a multi-lumen hose wherein the outer peripheral wall is not corrugated and that in such instance although the steps described above in connection with the manufacturing method of the present invention will be utilized except for the corrugating step. It will be further understood in accordance with the teachings of the present invention that the inner partition 27 in outer peripheral wall 26 of the hot parison 25 of FIG. 3 may be formed or extruded from a single plastic material, made together in a single extrusion step or pass, and thereafter a multi-lumen hose of the present invention may be manufactured using the above-described method of maintaining the inner partition substantially planar during the radially outward expansion and corrugation of the outer peripheral wall by using the above-described method of manufacture wherein the inner partition 14 is formed sufficiently thick to cause the greater decrease in thickness contiguously, at C in FIG. 9, to the peripheral wall 12 than medially as indicated at M in FIG. 9.

Figure 10:
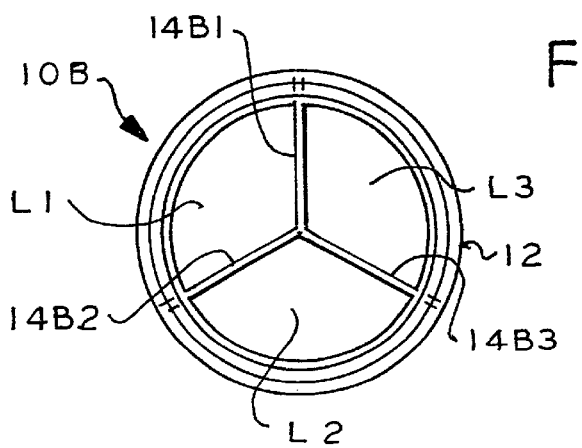
FIG. 10 is a diagrammatical illustration of a further embodiment of the present invention including a substantially planar inner partition including three substantially planar inner partition portions with respective ones thereof disposed at 120° with respect to each other to provide the hose with three lumen.

Referring further to the alternate embodiment multi-lumen hose of the present invention referred to generally above, alternate embodiment multi-lumen hose 10B shown in FIG. 10 includes a substantially planar inner partition including three substantially planar inner partition portions 14B1, 14B2 and 14B3 with adjacent ones of these inner partitions being disposed with respect to each other at an angle of about 120°. It will be understood that such three substantially planar inner partitions 14B1, 14B2 and 14B3 provide the hose 10B with three lumen L1, L2 and L3. Lumen L1, for example, may be used to communicate or deliver anesthesia gas or breathing gas such as oxygen or oxygen enriched air to a patient, lumen L2, for example, may be used to communicate exhalation gas away from the patient and back to either a ventilator or anesthesia machine, and the third lumen L3 may be used, for example, for the sampling of inspiratory and/or expiratory gases to and from a patient, for measuring end tidal $CO_2$, for testing for the presence of inhalation agents, for the indirect measurement of cardiac output, to measure inspiratory and expiratory airway pressure, or to sample and compare the $CO_2$ content of inspiratory gases to the patient with the $CO_2$ content of expiratory or exhalation gases from the patient.

Figure 11:
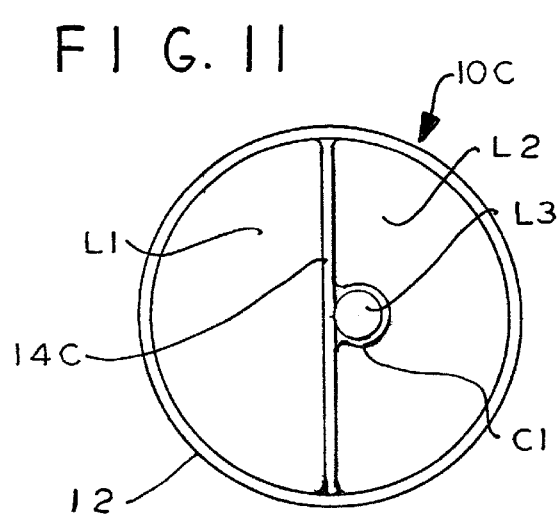
FIG. 11 is a further diagrammatical illustration of a further embodiment of multi-lumen hose of the present invention wherein the substantially planar inner partition divides the hose into first and second lumen and wherein such inner partition is provided with a longitudinally extending hollow cylindrical portion substantially along its mid portion providing the hose with another lumen.

In the alternate embodiment multi-lumen hose 10C of FIG. 11, the substantially planar inner partition 14C is a diametrical inner partition providing the hose 10C with two lumen L1 and L2 and in this embodiment the mid portion of the substantially planar inner partition 14C is provided with an integrally formed and longitudinally extending hollow cylindrical portion C1 providing the multi-lumen hose 10C with a third lumen L3. These lumen L1, L2 and L3 may be used, for example, in the same manner as the lumen L1, L2 and L3 described above with regard to multi-lumen hose 10B of FIG. 10.

Figure 12:
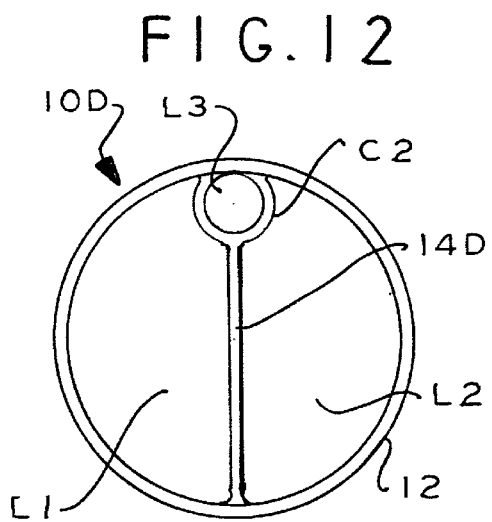
FIG. 12 is a diagrammatical illustration of a still further embodiment of the multi-lumen hose of the present invention wherein the end portion of the substantially planar inner partition comprises a longitudinally extending hollow cylindrical portion providing the hose with another lumen.

In the multi-lumen alternate embodiment hose 10D of FIG. 12, the substantially planar inner partition 14D is provided at one of its end portions with an integrally formed longitudinally extending hollow cylindrical portion or member C2 which provides the hose 10B with a third lumen L3 in addition to the two lumen L1 and L2 provided by the substantially planar diametrical inner partition 14D. These three lumen may be used similarly to the three lumen described above with regard to FIGS. 10 and 11.

Figure 13:
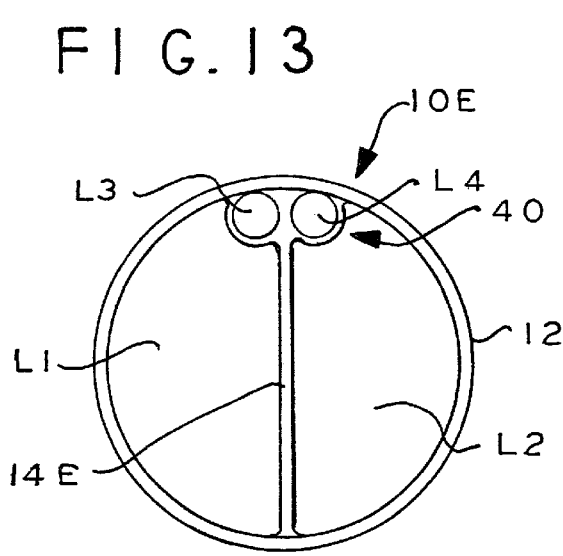
FIG. 13 is a diagrammatical illustration of a still further embodiment of the present invention wherein the substantially planar inner partition includes a portion at one of its ends including two longitudinally extending hollow cylindrical portions providing the hose with two additional lumen.
Figure 14:
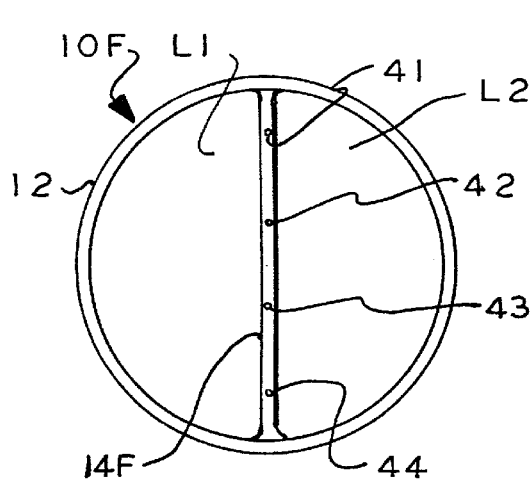
FIG. 14 is a diagrammatical illustration of a still further alternate embodiment of the present invention wherein the substantially planar inner partition is a thermal substantially planar inner partition for enhancing the transfer of heat between fluids flowing through the lumen of the hose, or for preventing, or at least substantially reducing, the formation of condensation in said hose from moisture carrying fluids flowing therethrough.

Referring to FIG. 13, the alternate embodiment multi-lumen hose 10E of the present invention may include a diametrically disposed substantially planar inner partition 14E dividing the hose into two lumen L1 and L2 and in this embodiment an end portion of the inner partition 14E may be formed integrally to include the integrally formed and longitudinally extending portion indicated by general numerical designation 40 providing the hose 14E with two additional lumen L3 and L4. Three of these lumen may be used in the same manner as the three lumen described above with regard to the multi-lumen hose 10B of FIG. 10, and the fourth lumen may be used for any other suitable purpose known to the multi-lumen hose art.

Referring lastly to the alternate embodiment multi-lumen hose 14F of FIG. 4, in this embodiment it will be understood that the diametrically disposed substantially planar inner partition 14F is a thermally conductive substantially planar inner partition to provide enhanced heat transfer between fluids flowing through the lumen L1 and L2 and/or to prevent, or at least substantially reduce, condensation of moisture from fluids flowing through the lumen L1 and L2, which condensation can unwontedly reside in the multi-lumen hose 10F. The thermally conductive substantially planar inner partition 14F may be made to be thermally conductive by having one or more thermally conductive wires 41, 42, 43 or 44 embedded therein as the substantially planar partition 14F is being formed or extruded as taught hereinabove with regard to FIG. 3. Alternatively, the substantially planar inner partition 14F may be made of suitable thermally conductive plastic of the type known to the art and coextruded separately from the outer peripheral wall as taught hereinabove with regard to the coextrusion manufacturing step described in connection with FIG. 3. Alternatively, it will be understood that thermally conductive wires, or other longitudinally extending thermally conductive material, may be inserted and reside in various of the smaller lumen shown in FIGS. 11–13.

It will be still further understood that the hose or tubing of the present invention in addition to being particularly useful in a medical application such as interconnecting a patient between an anesthesia machine or ventilator as described above in connection with the incorporated U.S. Pat. No. 5,121,756 also may be useful in other applications, such as industrial and commercial applications, as taught in the background of the invention of the incorporated U.S. Pat. No. 5,996,639.

It will be understood by those skilled in the art that many variations and modifications may be made in the present invention without departing form the spirit and the scope thereof.

What is claimed is:

1. A multi-lumen hose, comprising:

a corrugdted peripheral wall including an interior area and having an inner surface which defines a diemeter;

at least one substantially planrar inner partition extending from said inner surface across at least half of the diameter of said peripheral wall so as to divide said intertor area into a plurality of lumen, wherein said corrugated wall and substantially planar inner portion are formed by the steps of;

forming a hot multi-lumen parison, said parison including a hollow cylindrical peripheral portion with an inner surface defining a diameter of at least one substantially flat planar partition extending from said inner surface and across at least half of the diameter of said peripheral portion, said inner partition dividing an interior area pf said parison into a plurality of lumen;

expanding said peripheral portion radially outward to cause said inner partition to expand in width and to decrease in thickness medially and to decrease in thickness greater contiguously to said peripheral portion; and said greater decrease in thickness contiguously to said peripheral portion causing said inner partition to remain substantially planar upon expanding in width during radial expanding of said peripheral portion.

2. A multi-lumen hose, comprising:

a corrugated peripheral wall including an interior area and having an inner surface which defines a diameter;

at least one substantially planar inner partition extending substantially across the entirety of said diameter of said peripheral wall and providing said hose with first and second lumen, and wherein said substantially planar inner partition includes an end portion contiguous with said peripheral comprised of two cylindrical portions providing said hose with third and fourth lumen.

3. A multi-lumen hose, comprising:

a corrugated peripheral wall including an interior area and having an inner surface which defines a diameter;

at least one substantially planar diametrical inner partition extending across the entirety of said diameter of said peripheral wall and dividing said interior into two lumen, said substantially planar inner partition being a thermally conductive substantially planar inner partition for enhancing the transfer of heat between fluids flowing through said lumen or for reducing the formation of condensation in said hose, and wherein said thermally conductive substantially planar partition comprises a plastic substantially planar inner partition having at least one thermally conductive wire embedded therein.

4. A multi-lumen hose, comprising:

a corrugated peripheral wall including an interior area and having an inner surface which defines a diameter;

at least one substantially planar inner partition extending substantially across the entirety of said diameter of said peripheral wall and providing said hose with first and second lumen, and wherein said substantially planar inner partition includes a cylindrical end portion contiguous with said peripheral wall and providing said multi-lumen hose with a third lumen.

5. A multi-lumen hose, comprising:

a corrugated peripheral wall including an interior area and having an inner surface which defines a diameter;

a substantially planar inner partition extending from said inner surface across the diameter of said peripheral wall so as to divide said interior area into two lumen, and said substantially planar inner partition including a mid-portion provided with an integrally formed and longitudinally extending hollow cylindrical portion providing said multi-lumen hose with a third lumen.

* * * * *